United States Patent
Dohlman

(10) Patent No.: US 7,156,821 B2
(45) Date of Patent: Jan. 2, 2007

(54) SHUNT WITH ENCLOSED PRESSURE-RELIEF VALVE

(75) Inventor: Claes H. Dohlman, Weston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 11/104,952

(22) Filed: Apr. 13, 2005

(65) Prior Publication Data

US 2005/0240143 A1    Oct. 27, 2005

Related U.S. Application Data

(60) Provisional application No. 60/565,009, filed on Apr. 23, 2004, provisional application No. 60/626,190, filed on Nov. 9, 2004.

(51) Int. Cl.
*A61M 5/00*    (2006.01)
(52) U.S. Cl. .......................................................... 604/9
(58) Field of Classification Search ............. 604/8–10, 604/264, 523, 19, 27, 28, 30, 34, 48, 500, 604/507, 93.01, 164.01, 164.1, 164.11, 167.03, 604/246–47, 250, 533, 537, 284, 285, 288.01, 604/288.03
See application file for complete search history.

(56) References Cited

U.S. PATENT DOCUMENTS

| | | | |
|---|---|---|---|
| 3,949,750 A | 4/1976 | Freeman | |
| 4,554,918 A * | 11/1985 | White | 604/10 |
| 4,781,675 A | 11/1988 | White | |
| 4,915,684 A | 4/1990 | MacKeen et al. | |
| 4,959,048 A | 9/1990 | Seder et al. | |
| 5,283,063 A | 2/1994 | Freeman | |
| 5,346,464 A | 9/1994 | Camras | |
| 5,437,625 A | 8/1995 | Kurihashi | |
| 5,830,171 A | 11/1998 | Wallace | |
| 6,041,785 A | 3/2000 | Webb | |
| 6,077,299 A * | 6/2000 | Adelberg et al. | 623/24 |
| 6,083,188 A | 7/2000 | Becker | |
| 6,113,567 A | 9/2000 | Becker | |
| 6,261,256 B1 * | 7/2001 | Ahmed | 604/9 |
| 6,306,114 B1 | 10/2001 | Freeman et al. | |
| 6,508,779 B1 | 1/2003 | Suson | |
| 6,510,600 B1 | 1/2003 | Yaron et al. | |
| 6,544,208 B1 * | 4/2003 | Ethier et al. | 604/8 |
| 6,589,198 B1 | 7/2003 | Soltanpour et al. | |
| 6,682,500 B1 | 1/2004 | Soltanpour et al. | |
| 6,726,676 B1 | 4/2004 | Stegman et al. | |
| 2004/0215126 A1 * | 10/2004 | Ahmed | 604/9 |
| 2005/0119737 A1 | 6/2005 | Bene et al. | |

\* cited by examiner

*Primary Examiner*—Patricia Bianco
(74) *Attorney, Agent, or Firm*—Fish & Richardson P.C.

(57) ABSTRACT

A shunt for relief of intra-ocular pressure includes a pressure-relief valve and a jacket enclosing the pressure relief valve. When implanted on the sclera of an eye, the jacket protects the valve from interference by a capsule formed on the shunt.

19 Claims, 3 Drawing Sheets

SHUNT WITH ENCLOSED PRESSURE-RELIEF VALVE

RELATED APPLICATIONS

This application claims priority under 35 U.S.C. §119 from the U.S. Provisional Patent Applications 60/565,009, filed Apr. 23, 2004 and 60/626,190, filed Nov. 9, 2004.

FIELD OF INVENTION

The invention relates to ocular implants, and in particular, to implants for relieving excess intra-ocular fluid pressure.

BACKGROUND

The interior of the eye is bathed in a fluid often referred to as "aqueous" or "aqueous humor." This fluid is constantly being renewed. As additional fluid enters the eye, a corresponding amount of fluid must be drained from the eye to maintain a constant intra-ocular pressure. If the drainage of fluid cannot keep up with the entry of new fluid, the intra-ocular pressure will increase. If that pressure increases too much, the optic nerve will be damaged. This condition is often referred to as "glaucoma."

One way to relieve intra-ocular pressure is to implant a shunt having a one-way pressure-relief valve. When the intra-ocular pressure exceeds a threshold, the valve opens, and excess fluid drains onto a drainage bed. When the pressure drops sufficiently, the valve closes. This relieves the intra-ocular pressure.

Conventional shunts are designed to lead the fluid to the surrounding tissue. As a result, a capsule eventually forms over the valve and thereby interferes with its operation. This is particularly troublesome for patients who have an artificial cornea, (i.e., a keratoprosthesis).

SUMMARY

In one aspect, the invention includes a shunt for relief of intra-ocular pressure. The shunt has a pressure-relief valve having an inlet and an outlet, and an intake duct in fluid communication with the inlet. A jacket encloses the valve and forms a chamber for accumulation of fluid from the outlet. A drainage duct is disposed to direct fluid away from the chamber.

In another aspect, the invention includes a shunt for relief of intra-ocular pressure. The shunt includes a pressure-relief valve and a jacket that encloses the pressure relief valve. When implanted on the sclera of an eye, the jacket protects the valve from interference by a capsule formed on the shunt.

In one embodiment, the jacket is a silicone rubber jacket.

In another embodiment, the shunt includes an intake duct in fluid communications with the pressure-relief valve.

Another embodiment includes a drainage duct in fluid communication with the valve. The drainage duct can be configured for drainage into a fornix of a lower lid of an eye, into a nasal sinus cavity, or into a lacrimal sac.

In another embodiment, the jacket forms a chamber for accumulation of fluid from the pressure-relief valve. In this case, the drainage duct is in fluid communication with the chamber.

In another aspect, the invention includes a method for relieving intra-ocular pressure by enclosing a pressure-relief valve in a jacket; placing the jacket on the sclera; and leading fluid from inside the eye into a chamber defined by the jacket.

Practices of the invention include those that also include draining fluid away from the chamber.

Additional practices of the invention include those in which leading fluid from inside the eye includes leading fluid from the anterior chamber of the eye.

The fluid can be drained into any of a number of locations. For example, practices of the invention includes those in which fluid is drained into a fornix of a lower lid of an eye, a lacrimal sac, a nasal sinus cavity, a maxillary sinus cavity, an ethmoid sinus cavity, and any epithelial cavity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

These and other features and advantages of the invention will be apparent from the following detailed description and the accompanying figures, in which:

DETAILED DESCRIPTION

Figure 1:
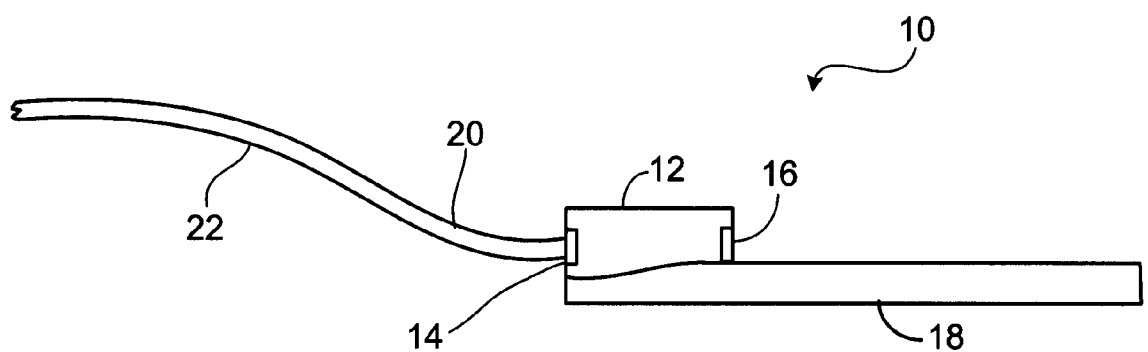
FIG. 1 is a conventional shunt.

A conventional glaucoma shunt 10, shown in FIG. 1, includes a valve 12 having a valve inlet 14 and a valve outlet 16. The valve outlet 16 is in fluid communication with a polypropylene drainage bed 18. The valve inlet 14 is in fluid communication with a proximal end 20 of an intake duct 22.

The valve 12 is a pressure-regulating valve that opens its outlet 16 whenever the fluid pressure at its inlet 14 is in excess of a pre-determined threshold. An exemplary valve 12 of this type is the Ahmed valve, which is manufactured by New World Medical, Inc. of Rancho Cucamonga, Calif.

In operation, the valve 12 and the drainage bed 18 are implanted onto the surface of the sclera of the eye. An open distal end of the intake duct 22 is inserted into the anterior chamber of the eye. Fluid, under pressure, fills the intake duct 22. When the pressure exceeds the pre-defined threshold, the valve outlet 16 opens. This causes the fluid to pass out of the valve 12 and over the drainage bed 18. The fluid is eventually absorbed by the surrounding tissue.

A difficulty that arises in the conventional shunt, particularly in those patients having a keratoprosthesis, is that a capsule slowly begins to form around the valve 12 and its associated drainage bed 18. This capsule eventually interferes with the shunt's ability to drain fluid.

Figure 2:
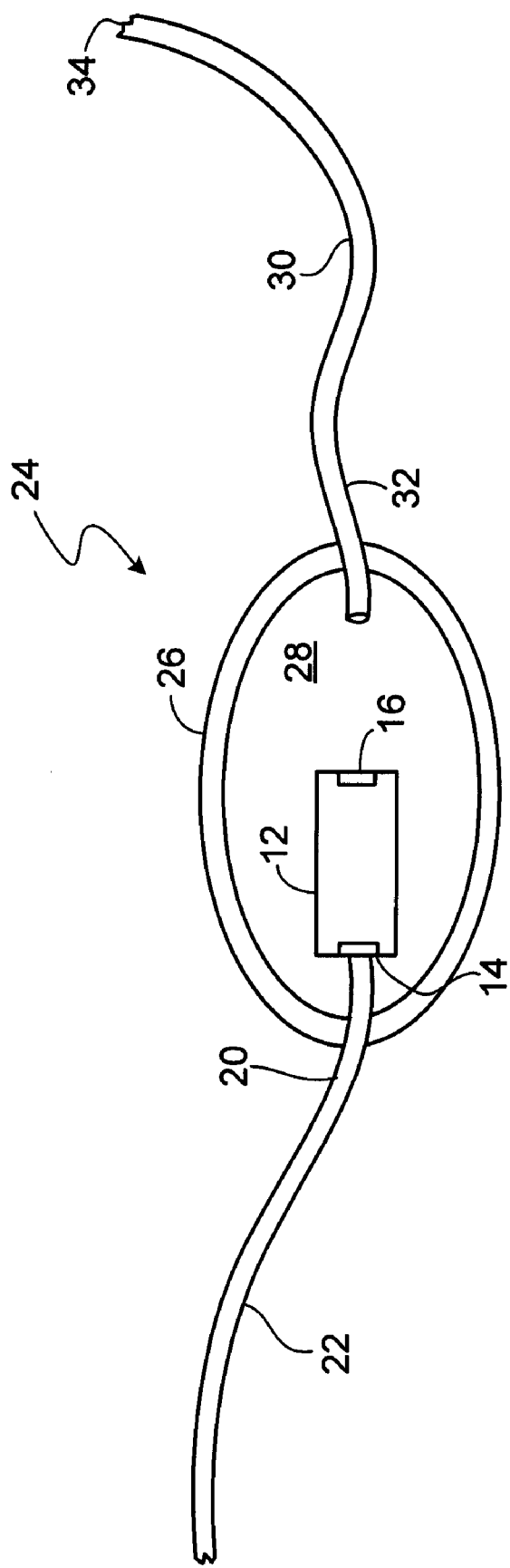
FIG. 2 is a jacketed shunt with a drainage duct.

A glaucoma shunt 24 incorporating the invention, as shown in FIG. 2, omits the drainage bed 18 and encloses the valve 12 in a silicone rubber jacket 26. In this case, fluid from the outlet 16 collects in a cavity 28 defined by the jacket 26.

Since the fluid is entrapped with the cavity 28, it can no longer drain into the surrounding tissue. To provide the necessary drainage, the shunt 24 includes a drainage duct 30 having a proximal end 32 and a distal end 34. The proximal end 32 of the drainage duct 30 is placed in fluid communication with the cavity 28. The distal end 34 is inserted into a nearby epithelial cavity. This enables fluid that collects in the cavity 28 to be drained into a nearby epithelial cavity, such as the maxillary sinus.

A preferred epithelial cavity for receiving the distal end 34 of the drainage duct 30 is the maxillary sinus. However, the distal end 34 of the drainage duct 30 may also be inserted into the fornix of the lower lid, the lacrimal sac, or the ethmoid sinus.

Because the valve 12 in FIG. 2 is enclosed in a jacket 26, the capsule that would normally interfere with the leaching of fluid into surrounding tissue now forms outside the jacket 26. As a result, it no longer interferes with fluid flow, as was the case with the shunt 10 in FIG. 1.

Materials other than silicone rubber can be used to form a jacket 26 around the valve 12. What is necessary is that the jacket material be biocompatible and that it be impervious to water.

Figure 3:
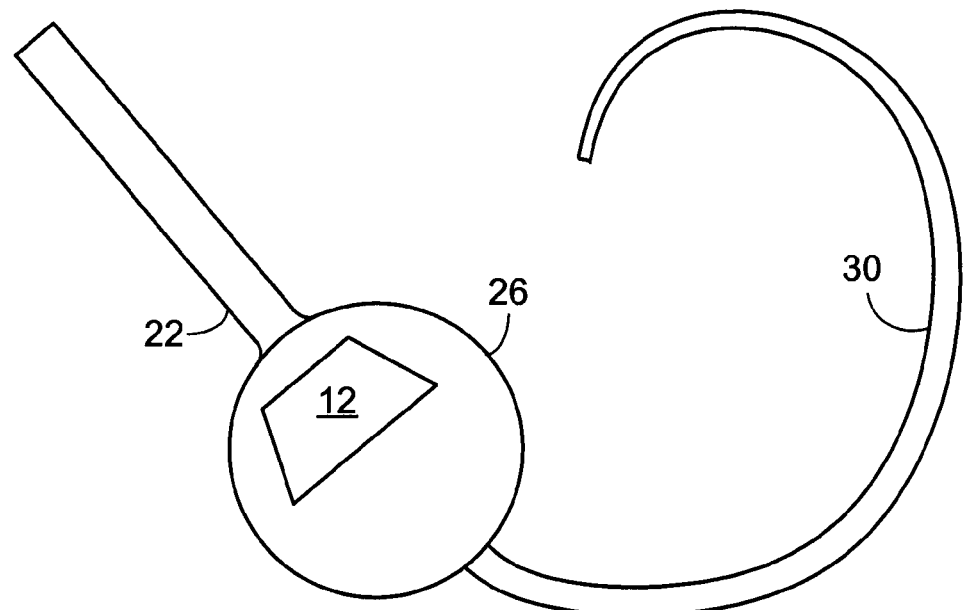
FIG. 3 is a jacketed shunt with a drainage duct for drainage into a sinus cavity.
Figure 4:
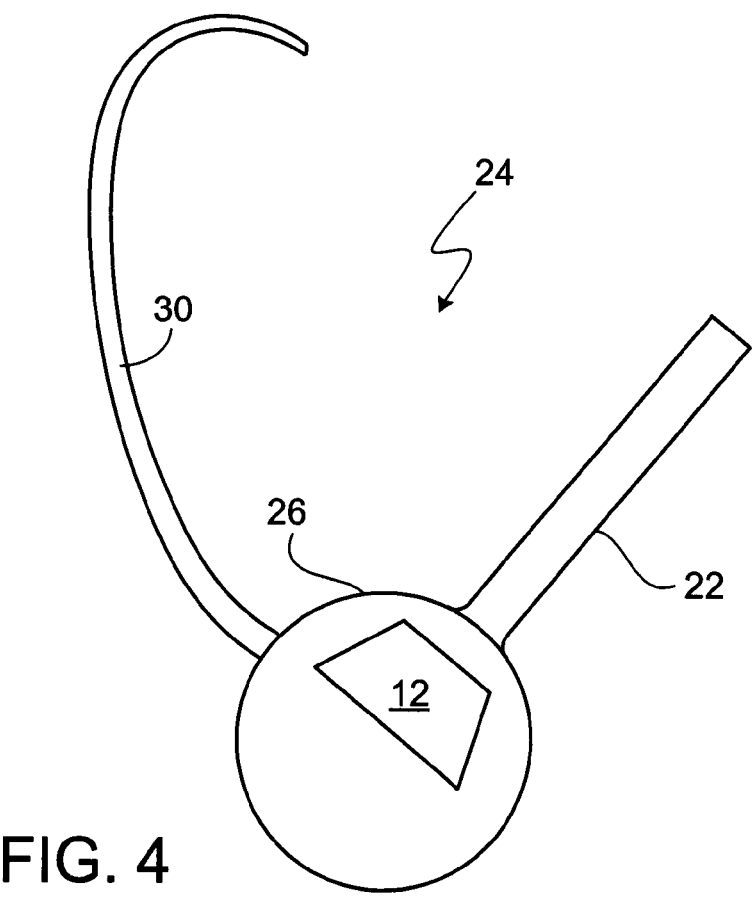
FIG. 4 is a jacketed shunt with a drainage duct for drainage into the fornix behind the lower lid of the eye.

The shape of the drainage duct 30 can vary depending on where it is to be inserted. In one embodiment, shown in FIG. 2, the drainage duct 30 is intended to extend into the maxillary sinus cavity. However, the drainage duct 30 can also be configured, as shown in FIG. 3, for extending into the fornix of the lower eyelid.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A shunt for relief of intra-ocular pressure, the shunt comprising:
   a pressure-relief valve having an inlet and an outlet;
   an intake duct in fluid communication with the inlet;
   a jacket enclosing the valve, the jacket forming a chamber for accumulation of fluid from the outlet; and
   a drainage duct in direct fluid communication with the chamber.

2. A shunt for relief of intra-ocular pressure, the shunt comprising:
   a pressure-relief valve;
   a jacket enclosing the pressure relief valve, whereby, when implanted on the sclera of an eye, the jacket protects the valve from interference by a capsule formed on the shunt; and
   a drainage duct in direct fluid communication with the jacket.

3. The shunt of claim 2, further comprising a drainage duct in fluid communication with the valve.

4. The shunt of claim 3, wherein the drainage duct is configured for drainage into a fornix of a lower lid of an eye.

5. The shunt of claim 3, wherein the drainage duct is configured for drainage into a nasal sinus cavity.

6. The shunt of claim 3, wherein the jacket forms a chamber for accumulation of fluid from the pressure-relief valve, and wherein the drainage duct is in fluid communication with the chamber.

7. The shunt of claim 3, wherein the drainage duct is configured for drainage into a lacrimal sac.

8. The shunt of claim 3, wherein the drainage duct in configured for drainage into the ethmoid sinus.

9. The shunt of claim 3, wherein the drainage duct in configured for drainage into the maxillary sinus.

10. The shunt of claim 2, wherein the jacket comprises silicone rubber.

11. The shunt of claim 2, wherein the jacket comprises a material impermeable to water.

12. The shunt of claim 2, further comprising an intake duct in fluid communication with the pressure-relief valve.

13. A method for relieving intra-ocular pressure, the method comprising:
   enclosing a pressure-relief valve in a jacket;
   placing the jacket on the sclera; and
   leading fluid from inside the eye into a chamber defined by the jacket; and
   draining accumulated fluid from inside the chamber through a duct leading away from the chamber, wherein the duct is directly connected to the chamber.

14. The method of claim 13, wherein draining fluid away from the chamber comprises draining fluid into a nasal sinus cavity.

15. The method of claim 14, wherein draining fluid into a sinus cavity comprises draining fluid into a sinus cavity selected from the group consisting of a maxillary sinus cavity and an ethmoid sinus cavity.

16. The method of claim 13, wherein leading fluid from inside the eye comprises leading fluid from the anterior chamber of the eye.

17. The method of claim 13, wherein draining fluid away from the chamber comprises draining fluid into a fornix of a lower lid of an eye.

18. The method of claim 13, wherein draining fluid away from the chamber comprises draining fluid into a lacrimal sac.

19. The method of claim 13, wherein draining fluid away from the chamber comprises draining fluid into an epithelial cavity.

* * * * *